US006426437B1

(12) United States Patent
Shum

(10) Patent No.: US 6,426,437 B1
(45) Date of Patent: Jul. 30, 2002

(54) HYDROFORMYLATION PROCESS

(75) Inventor: Wilfred P. Shum, West Chester, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/735,678

(22) Filed: Dec. 13, 2000

(51) Int. Cl.$^7$ .......................... C07C 27/04; C07C 27/00
(52) U.S. Cl. ....................... 568/862; 568/861
(58) Field of Search ................ 568/860, 861, 568/862

(56) References Cited

U.S. PATENT DOCUMENTS

| | | | | |
|---|---|---|---|---|
| 4,215,077 A | * | 7/1980 | Matsumoto et al. | 568/454 |
| 4,238,419 A | | 12/1980 | Matsumoto et al. | 568/454 |
| 4,678,857 A | | 7/1987 | Dureanleau et al. | 568/454 |
| 5,290,743 A | | 3/1994 | Chang | 502/30 |
| 5,504,261 A | | 4/1996 | Mullin et al. | 568/862 |
| 5,817,848 A | * | 10/1998 | Kamer et al. | 556/12 |
| 5,874,652 A | * | 2/1999 | Pitchai et al. | 568/881 |
| 6,127,584 A | * | 10/2000 | Zajacek et al. | 568/852 |

FOREIGN PATENT DOCUMENTS

JP S52-78809 7/1977

OTHER PUBLICATIONS

Casey et al., J. Am. Chem. Soc., 1995, 117, pp. 6007–6014.*
Casey, et al., *J. Am. Chem. Soc.,* 1995, 117.
van der Veen, et al., *Organomet.,* 1999, 18, 4765.

* cited by examiner

*Primary Examiner*—Johann Richter
*Assistant Examiner*—Elvis O. Price
(74) *Attorney, Agent, or Firm*—Kevin M. Carroll

(57) ABSTRACT

A process for the production of 1,4-butanediol is described. The process comprises hydroformylating allyl alcohol in the presence of a solvent and a catalyst system comprising a rhodium complex, a ruthenium complex and a diphosphine ligand and hydrogenating the resulting 4-hydroxybutyraldehyde using the same catalyst system. The process gives high yield of 1,4-butanediol compared to 2-methyl-1,3-propanediol.

12 Claims, No Drawings

HYDROFORMYLATION PROCESS

FIELD OF THE INVENTION

This invention relates to a process for the production of 1,4-butanediol from allyl alcohol using a catalyst system comprising a rhodium complex, a ruthenium complex and a diphosphine ligand. The catalyst system is useful in both the hydroformylation step (allyl alcohol to 4-hydroxybutyraldehyde) and the hydrogenation step (4-hydroxybutyraldehyde to 1,4-butanediol). Surprisingly, the catalyst system shows high activity and produces a high ratio of linear:branched (1,4-butanediol:2-methyl-1,3-propanediol) product. The catalyst is also easily recycled with minimal loss of activity.

BACKGROUND OF THE INVENTION

The production of 1,4-butanediol from allyl alcohol is a well-known and commercially practiced process. See, for example, U.S. Pat. Nos. 4,238,419, 4,678,857, 4,215,177, 5,290,743 and the like. Generally, the process consists of a hydroformylation reaction followed by hydrogenation step. In hydroformylation, allyl alcohol is reacted with a $CO/H_2$ gas mixture using a rhodium-phosphine catalyst system to form 4-hydroxybutyraldehyde. Then, the 4-hydroxybutyraldehyde is separated from the catalyst by water extraction and hydrogenated over a nickel catalyst to form 1,4-butanediol. See U.S. Pat. No. 5,504,261.

The above reaction sequence involves the use of different catalysts and usually different reaction gas mixtures for each of the reactions. For obvious reasons, it would be advantageous to produce 1,4-butanediol from allyl alcohol using only a single catalyst system.

It has been reported, for example, in Kokai No. S52-78809 by Kawahito, et al. that 1,4-butanediol can be produced from allyl alcohol in a one-step reaction system using a rhodium and a trialkyl phosphine catalyst system. However, a disadvantage of the process described in S52-78809 is the relatively low ratio of 1,4-butanediol to 2-methyl-1,3-propanediol which is produced. U.S. Pat. No. 6,127,584 also discloses a one catalyst process using rhodium and a trialkyl phosphine wherein higher ratios of 1,4-butanediol to 2-methyl-1,3-propanediol are produced. However, this process also produces a significant amount of isobutanol by-product, which has little commercial value.

In sum, new processes that would allow the production of 1,4-butanediol using a single catalyst system are needed. Particularly valuable processes would result in high ratios of 1,4-butanediol (BDO) compared to 2-methyl-1,3-propanediol (MPD), without production of isobutanol by-product.

SUMMARY OF THE INVENTION

The invention is a process for producing 1,4-butanediol that comprises first reacting allyl alcohol with a mixture of carbon monoxide and hydrogen in the presence of a solvent and a catalyst system to produce 4-hydroxybutyraldehyde. The catalyst system comprises a rhodium complex, a ruthenium complex and a bidentate diphosphine ligand. The 4-hydroxybutyraldehyde is then reacted with hydrogen in the presence of the catalyst system and the solvent to form 1,4-butanediol. The 1,4-butanediol product is optionally separated from the solvent and the catalyst system by water extraction. The solvent and catalyst system are then optionally recycled to the first step. I surprisingly found that using this catalyst system produced high BDO:MPD ratio with no isobutanol by-product.

DETAILED DESCRIPTION OF THE INVENTION

The process of the invention comprises a hydroformylation step followed by a hydrogenation step. The hydroformylation step comprises reacting allyl alcohol with a mixture of carbon monoxide and hydrogen in the presence of a solvent and a catalyst system to produce 4-hydroxybutyraldehyde. The hydrogenation step follows hydroformylation and comprises reacting the 4-hydroxybutyraldehyde with hydrogen in the presence of the catalyst system and solvent.

The catalyst system of the invention comprises a rhodium complex, a ruthenium complex and a bidentate diphosphine ligand. Suitable rhodium complexes contain rhodium attached to ligand groups. The rhodium complex is soluble in the solvent. There are no particular restrictions regarding the choice of ligands attached to the rhodium complex. For example, suitable ligands include halides, hydrides, carbonyl, substituted and unsubstituted cyclopentadienyls, 2,4-alkanedionates, and trialkyl or triaryl phosphines. Particularly preferred ligands include chloride, carbonyl, acetylacetonate (2,4-pentanedionate), and triphenylphosphine.

The catalyst system of the invention also comprises a ruthenium complex. Suitable ruthenium complexes contain ruthenium attached to ligand groups. The ruthenium complex is soluble in the solvent. There are no particular restrictions regarding the choice of ligands attached to the ruthenium complex. For example, suitable ligands include halides, hydrides, carbonyl, trialkyl or triaryl phosphines, substituted and unsubstituted cyclopentadienyls, and 2,4-alkanedionates. Particularly preferred ligands include chloride, carbonyl, triphenylphosphine, cyclopentadienyl, and acetylacetonate (2,4-pentanedionate).

The catalyst system of the invention also comprises a diphosphine ligand. Diphosphine ligands contain two phosphine atoms that are covalently bond to one another through a bridging groups that contains at least one nonhydrogen atom. Diphosphine ligands are well known in the art. Examples of suitable diphosphine ligands include DIOP [2,3-O-isopropylidene-2,3-dihydroxy-1,4-bis (diphenylphosphino)butane], XANTPHOS [4a,9a-dihydro-9,9-dimethyl-4,5-bis(diphenylphosphino)xanthene], DIPHOS [1,2-bis(diphenylphospino)ethane], BISBI [2,2'-bis((diphenylphospino)methyl-1,1'-biphenyl], T-BDCP [trans-1,2-bis((diphenylphospino)methyl)cyclopropane], and CHDIOP (see, for example, Casey, et al., *J. Am. Chem. Soc.*, 1995, 117, 6007, van der Veen, et al., *Organomet.*, 1999, 18, 4765, and U.S. Pat. No. 5,817,848). Preferred diphosphine ligands include DIOP and XANTPHOS.

The diphosphine ligand can be pre-associated with the rhodium complex and/or ruthenium complex prior to use, or added separately. However, it is preferable to add the diphosphine ligand separate from the rhodium and ruthenium complexes.

The molar ratio of Rh:Ru contained in the catalyst system is not critical. A typical Rh:Ru molar ratio ranges from 5:1 to 1:5, preferably from 2:1 to 1:2, and most preferably the molar ratio is 1. The amount of diphosphine ligand is typically added such that the molar ratio of diphosphine ligand:(Rh+Ru) ranges from 2 to 20, preferably from 2 to 6, and most preferably the molar ratio is 4.

A solvent is also required for the process of the invention. Typical solvents are those that are capable of solubilizing the rhodium and ruthenium complexes and are not reactive to the hydroxyaldehydes that are produced in the hydroformylation step. Suitable solvents include any organic solvent having very low or minimal solubility in water. Preferred solvents include $C_4$–$C_{20}$ aliphatic hydrocarbons, $C_1$–$C_{20}$ halogenated aliphatic hydrocarbons, $C_6$–$C_{20}$ aromatic hydrocarbons, $C_6$–$C_{20}$ halogenated aromatic hydrocarbons, and ethers. Particularly preferred solvents include toluene, cyclohexane, and methyl t-butyl ether.

Typical reaction conditions for the hydroformylation step are mild to favor the formation of linear rather than branched reaction products. Reaction conditions are typically in the range of from about 20 to 100° C. and pressures of from about 30 to 600 psig, preferably from about 60 to 80° C. and 30 to 300 psig. The molar ratio of $CO:H_2$ is typically about 1:1, although the ratio can vary considerably. The partial pressure of CO is typically within the range of 50 to 100 psig. The partial pressure of hydrogen is typically within the range of 50 to 100 psig. The reaction is conducted at these conditions until a predominance of the allyl alcohol has reacted, e.g. 60 to 90%, the products being largely 4-hydroxybutyraldehyde with some BDO and branched reaction products. Usually a reaction time of 1 to 4 hours is adequate.

Following the hydroformylation step, the first product mixture comprising 4-hydroxybutyraldehyde, the solvent and the catalyst system is transferred to another vessel for hydrogenation of the 4-hydroxybutyraldehyde. Prior to hydrogenation, it may be desirable to remove the residual CO and $H_2$ remaining after hydroformylation. Hydrogen is added to the vessel for the hydrogenation. The hydrogenation reaction conditions are typically more severe than hydroformylation. Reaction conditions are typically in the range of from about 60 to 200° C. and pressures of from about 200 to 1000 psig, preferably from about 80 to 140° C. and 300 to 1000 psig. Generally reaction times of 1 to 10 hours are appropriate. Preferably, water can also be added to the hydrogenation vessel. The addition of a small amount of water, typically from about 0.1 to about 5 weight percent of the total amount of the first reaction mixture added to hydrogenation, has been shown to slightly improve selectivity to BDO product (see Example 2).

During the hydrogenation reaction, BDO is formed while the high ratio of linear to branched products is substantially retained. Thus, the second product mixture comprises BDO, the solvent and the catalyst system. After hydrogenation, the second product mixture and water are optionally passed to an extraction vessel for a water extraction step in which BDO is separated from the solvent and catalyst system by water extraction. Water extraction methods are well known in the art and can be effected by any suitable means, such as mixer-settlers, packed or trayed extraction columns, rotating disk contactors, or passed to a settling tank for resolution of the mixture into aqueous and organic phases. BDO remains soluble in the water (aqueous) phase and the catalyst mixture remains in the solvent (organic) phase. The extraction step is necessary to separate the catalyst system from the BDO product.

The organic (solvent) phase, containing a major proportion of the catalyst system, is optionally recycled to the hydroformylation step for further reaction with allyl alcohol. The aqueous phase comprises BDO, MPD, GBL, and ether dimers formed from the reaction of hydroxyaldehydes. BDO, MPD, and GBL are commercially significant products. It may be necessary to further process the aqueous stream in order to break up the ether dimers that are formed. This reaction can be easily performed by the hydrogenation of the aqueous stream in the presence of a suitable hydrogenation catalyst. Suitable hydrogenation catalysts include any Group VII metal, such as nickel, cobalt, ruthenium, platinum, and palladium, as well as copper, zinc and chromium and mixtures and alloys thereof. Especially preferred are fixed-bed nickel catalysts. Temperatures for this finishing hydrogenation reaction are typically greater than 40° C., preferably from 40–200° C. Hydrogen pressure is at least 100 psig and typically from about 200 to 2000 psig.

In an illustrative embodiment of the invention, allyl alcohol, solvent such as toluene, and the catalyst system are charged to a first reactor to which is introduced the $CO/H_2$ reaction gas mixture. The reactor is heated to reaction temperature and pressurized with the $CO/H_2$ mixture for the desired reaction time to form 4-hydroxybutanol with high selectivity. Preferably, agitation is provided.

Thereafter, the product effluent from hydroformylation is transferred to a second reactor. The remaining CO and $H_2$ from hydroformylation may be optionally removed during transfer. $H_2$ is introduced into the reactor and the temperature of the reaction mixture is increased along with $H_2$ pressure to the more severe conditions for BDO formation. These conditions are maintained until the desired conversion to BDO is achieved.

The product mixture following hydrogenation can then be separated by extraction of the diol products into water. The catalyst system remains in the solvent (organic) phase, which can then be recycled to the first reactor for hydroformylation of allyl alcohol.

The product of this reaction typically contains BDO, MPD (BDO:MPD=4), γ-butyrolactone (GBL), and ether dimers. GBL is a commercially useful product that is currently produced from BDO. The ether dimers (reaction products of hydroxybutyraldehydes and diols) can be converted into BDO by a finishing hydrogenation reactor, so that overall selectivity to BDO product is even further increased. No isobutanol is made by this process.

The following examples merely illustrate the invention. Those skilled in the art will recognize many variations that are within the spirit of the invention and scope of the claims.

EXAMPLE 1

PREPARATION OF BDO FROM Ru/Rh CATALSYT SYSTEM

Example 1A: Allyl alcohol (6.5 g), toluene (30 g), $Rh(CO)_2(acac)$ (0.02 g), $[RUCl_2(CO)_3]_2$ (0.02 g), and DIOP (0.16 g) are charged into a 100 mL Parr reactor for hydroformylation. After 3 hours at 65° C. and under 200 psig of $CO/H_2$, allyl alcohol conversion is >98%. The reaction effluent is then transferred into another Parr reactor for hydrogenation. After 3 hours at 100° C. and under 400 psig of $H_2$, the entire reaction effluent (now 2 phases due to limited solubility of BDO in toluene) is removed from the reactor and extracted with 50 ml of water for product recovery. The products in the two phases were analyzed by gas chromatography (GC). Conversion of hydroxyaldehydes (HBA and HMPA) is 95%, and the product selectivities are: 57% BDO, 14% MPD, 19% GBL, and 10% ether dimers.

Example 1B: Example 1B is run according to the procedure of Example 1A except that chloro(cyclopentadienyl) bis(triphenylphosphine) ruthenium (II) (0.056 g) is used in place of $[RuCl_2(CO)_3]_2$. Hydroxyaldehydes conversion is 96% and product selectivities are: 56% BDO, 14% MPD, 20% GBL, and 10% ether dimers.

Example 1C: Example 1C is run according to the procedure of Example 1A except that dichlorocarbonylbis (triphenylphosphine) ruthenium (II) (0.058 g) is used in place of $[RuCl_2(CO)_3]_2$. Hydroxyaldehydes conversion is 95% and product selectivities are: 56% BDO, 14% MPD, 20% GBL, and 10% ether dimers.

Example 1D: Example 1D is run according to the procedure of Example 1A except that carbonyl(dihydrido)tris(triphenylphosphine) ruthenium (II) (0.071 g) is used in place of [RuCl$_2$(CO)$_3$]$_2$. Hydroxyaldehydes conversion is 88% and product selectivities are: 54% BDO, 14% MPD, 23% GBL, and 9% ether dimers.

EXAMPLE 2

EFFECT OF WATER ADDITION TO THE HYDROGENATION STEP DURING BDO PREPARATION

Example 2 is run according to the procedure of Example 1A except that water (2 g) is added to the first reaction mixture prior to hydrogenation. Conversion of hydroxyaldehydes is 95%, and the product selectivities are: 63% BDO, 14% MPD, 15% GBL, and 8% ether dimers.

COMPARATIVE EXAMPLE 3

USE OF TRIPHENYLPHOSPINE IN PLACE OF A DISPHOSHPHINE LIGAND

Allyl alcohol (6.5 g), toluene (30 g), Rh(CO)$_2$(acac) (0.02 g), [RuCl$_2$(CO)$_3$]$_2$ (0.02 g), and triphenylphosphine (2.0 g) are charged into a 100 mL Parr reactor for hydroformylation. After 3 hours at 65° C. and under 200 psig of CO/H$_2$, allyl alcohol conversion is 99%. The reaction effluent is then transferred into a second Parr reactor for hydrogenation. After 6 hours at 100° C. and under 400 psig of H$_2$, the reaction effluent is removed from the reactor and extracted with 50 ml of water for product recovery. The products in the two phases were analyzed by gas chromatography (GC). Conversion of hydroxyaldehydes is less than 50%, and the product selectivities are: 32% BDO, 18% MPD, 22% GBL, and 20% ether dimers, with 8% unknown heavies.

I claim:

1. A process for producing 1,4-butanediol comprising the steps of:
   (a) reacting allyl alcohol with a mixture of carbon monoxide and hydrogen in the presence of a solvent and a catalyst system comprising a rhodium complex, a ruthenium complex and a bidentate diphosphine ligand to produce a first product mixture comprising 4-hydroxybutyraldehyde, the solvent and the catalyst system, wherein the ratio of diphosphine ligand:(rhodium complex+ruthenium complex) is at least two;
   (b) reacting the first product mixture with hydrogen to form a second product mixture comprising 1,4-butanediol, the solvent and the catalyst system;
   (c) optionally, separating 1,4-butanediol from the solvent and the catalyst system by water extraction, whereby a water phase and a solvent phase are formed, wherein the water phase comprises 1,4-butanediol the solvent phase comprises the solvent and the catalyst system; and
   (d) optionally, recycling the solvent phase to step (a).

2. The process of claim 1 wherein the solvent is toluene, cyclohexane, and methyl t-butyl ether.

3. The process of claim 1 wherein the rhodium complex comprises rhodium and ligands selected from the group consisting of halides, hydrides, carbonyl, trialkyl or triaryl phosphines, substituted and unsubstituted cyclopentadienyls, and 2,4-alkanedionates.

4. The process of claim 1 wherein the ruthenium complex comprises ruthenium and ligands selected from the group consisting of halides, hydrides, carbonyl, trialkyl or triaryl phosphines, substituted and unsubstituted cyclopentadienyls, and 2,4-alkanedionates.

5. The process of claim 1 wherein the diphosphine ligand is selected from the group consisting of DIOP and XANTHOS.

6. The process of claim 1 wherein step (a) is performed at a temperature of from about 60° C. to about 80° C. and a pressure of from about 30 to about 300 psig.

7. The process of claim 1 wherein step (b) is performed at a temperature of from about 80° C. to about 140° C. and a pressure of from about 300 to about 1000 psig.

8. The process of claim 1 wherein the carbon monoxide and hydrogen used in step (a) are removed prior to step (b).

9. The process of claim 1 wherein water is added to step (b).

10. The process of claim 1 comprising an additional step of reacting the water phase from step (c) with hydrogen in the presence of a hydrogenation catalyst comprising a Group VIII metal.

11. The process of claim 10 wherein the hydrogenation catalyst is a fixed-bed nickel catalyst.

12. A process for producing 1,4-butanediol comprising the steps of:
   (a) reacting allyl alcohol with a mixture of carbon monoxide and hydrogen in the presence of a solvent and a catalyst system comprising a rhodium complex, a ruthenium complex and a bidentate diphosphine ligand to produce a first product mixture comprising 4-hydroxybutyraldehyde, the solvent and the catalyst system, wherein the ratio of diphosphine ligand:(rhodium complex+ruthenium complex) is at least two;
   (b) reacting the first product mixture with hydrogen to form a second product mixture comprising 1,4-butanediol, the solvent and the catalyst system;
   (c) separating 1,4-butanediol from the solvent and the catalyst system by water extraction, whereby a water phase and a solvent phase are formed, wherein the water phase comprises 1,4-butanediol the solvent phase comprises the solvent and the catalyst system;
   (d) recycling the solvent phase to step (a); and
   (e) reacting the water phase from step (c) with hydrogen in the presence of a hydrogenation catalyst comprising a Group VIII metal.

* * * * *